US007740356B2

United States Patent
Sarver

(10) Patent No.: US 7,740,356 B2
(45) Date of Patent: Jun. 22, 2010

(54) MONOCHROMATIC MULTI-RESOLUTION CORNEAL TOPOGRAPHY TARGET

(75) Inventor: Edwin J. Sarver, Carbondale, IL (US)

(73) Assignee: Sarver & Associates, Inc., Carbondale, IL (US)

(*) Notice: Subject to any disclaimer, the term of this patent is extended or adjusted under 35 U.S.C. 154(b) by 0 days.

(21) Appl. No.: 12/357,002

(22) Filed: Jan. 21, 2009

(65) Prior Publication Data
US 2009/0185134 A1    Jul. 23, 2009

Related U.S. Application Data

(60) Provisional application No. 61/022,419, filed on Jan. 21, 2008.

(51) Int. Cl.
*A61B 3/10* (2006.01)

(52) U.S. Cl. .................................. 351/212; 351/221
(58) Field of Classification Search .............. 351/210, 351/212, 221, 247
See application file for complete search history.

(56) References Cited

U.S. PATENT DOCUMENTS

| 5,668,623 | A | * | 9/1997 | Sakurai et al. | ............ 351/212 |
| 6,116,738 | A | * | 9/2000 | Rorabaugh | ............ 351/247 |
| 6,926,408 | B2 | | 8/2005 | Sarver | |

* cited by examiner

*Primary Examiner*—Huy K Mai
(74) *Attorney, Agent, or Firm*—McHale & Slavin, P.A.

(57) ABSTRACT

A method to encode both high-resolution and low-resolution reflected features of a cornea to improve the measurements for reflection based corneal topography systems. The corneal topography reflective target provides for multiple resolutions of measurements to be obtained from a single acquisition.

20 Claims, 6 Drawing Sheets

MONOCHROMATIC MULTI-RESOLUTION CORNEAL TOPOGRAPHY TARGET

RELATED APPLICATIONS

This application claims the benefit under 35 U.S.C. 119(e) of U.S. Provisional Patent Application No. 61/022,419 filed Jan. 21, 2008, entitled MONOCHROMATIC MULTIRESOLUTION CORNEAL TOPOGRAPHY TARGET, the entirety of which is incorporated herein by reference. This application is also related to U.S. Pat. No. 6,926,408, the contents of which are hereby incorporated by reference.

FIELD OF THE INVENTION

This invention is directed to the field of eye examination.

BACKGROUND OF THE INVENTION

The human cornea provides about two-thirds of the refraction of the eye. Thus, its shape is of great interest to optometrists and ophthalmologists who must provide a patient with sharp vision. Although there are various methods to measure the corneas, the most popular commercial systems are based of the principle of measuring a pattern reflected off the cornea. The pattern most often used for this purpose is a set of concentric rings. One problem with concentric ring patterns is that it is difficult to know the exact point of correspondence between a point on the reflected pattern source and its image reflected off the cornea. If the cornea is not axially symmetric, the surface normal of a point on the cornea will not lie in the meridional plane of the measurement system and thus, the point of light originating on the reflected pattern source will not lie in the same meridional plane. To directly measure the point of correspondence, polar and rectangular checkerboard patterns have also been proposed, but have not become popular in commercial systems.

One problem with this polychromatic target approach is that color cameras or multiple band pass cameras must be used in the system. This increases the parts and manufacturing cost associated with the instrument. To overcome this limitation, we present a monochromatic multi-resolution target that provides most of the benefits of the polychromatic multi-resolution target, but reduces the parts and manufacturing costs so that the instrument is more competitive in the commercial marketplace.

A corneal topography system measures the power and shape of the cornea so that a clinician can use this information to evaluate or treat a patient's vision. One of the most popular methods for measuring this corneal information involves reflecting a light target off the cornea. By analyzing an image of the reflected target, the power and shape of the cornea can be determined. In our previous patent U.S. Pat. No. 6,926,408 we described why a polychromatic multi-resolution corneal topography target can help improve on corneal measurements.

The instant invention relates to a corneal topography system that measures the power and shape of the cornea so that a clinician can use this information to evaluate or treat a patient's vision. One of the most popular methods for measuring this corneal information involves reflecting a light target off the cornea. By analyzing an image of the reflected target, the power and shape of the cornea can be determined. In applicants' U.S. Pat. No. 6,926,408, it was described why a polychromatic multi-resolution corneal topography target can help improve on corneal measurements.

The instant invention provides a method to encode both high-resolution and low-resolution reflected images of a cornea to improve the measurements for reflection based corneal topography systems.

SUMMARY OF THE INVENTION

This corneal topography reflective target provides a simple method and apparatus to encode both high-resolution and low-resolution reflected features of a cornea to improve the measurements for reflection based corneal topography systems.

Accordingly, it is an objective of the instant invention is to disclose a corneal topography reflective target that provides for multiple (two or more) resolutions of measurements to be obtained from a single acquisition.

It is a further objective of the instant invention to disclose the processing of the multi-resolution captured image separates the resolutions so that both short radius of curvature (high optical power corneas) and long radius of curvatures (low optical power corneas) may be adequately measured by the system It is yet another objective of the instant invention is to disclose the reconstruction of the surface using a variable step size algorithm to accommodate varying resolution across the measured surface.

It is a still further objective of the invention is to disclose a corneal topography reflective target where the source illumination is monochromatic to yield an economical system.

Still another objective of the invention is to disclose a corneal topography reflective target where the processing of the captured target reflection image where both edge and peak detection is employed to increase the total number of measurements from the multi-resolution pattern over use of edges or peaks alone.

Yet another objective of the invention is to disclose a corneal topography reflective target where the target is implemented using an electro luminescent back light.

Another objective of the invention is to disclose a corneal topography reflective target where the target is implemented using a diffuse back light and a transparent overlay.

Still another objective of the invention is to disclose a corneal topography reflective target where the individual rings may be turned on and off either individually or as a group.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
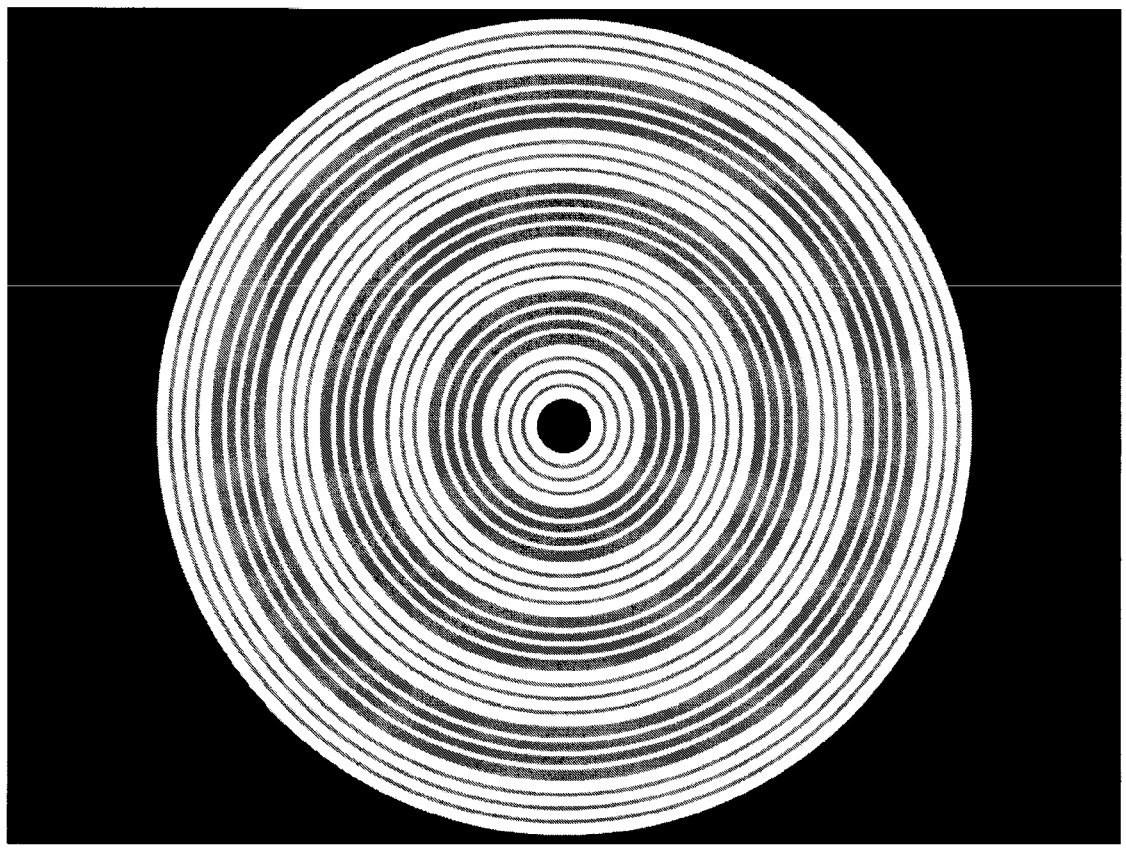
FIG. 1 is a simulated captured image for a corneal topography system using a monochromatic multi-resolution target.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

A simulated captured image for a corneal topography system using the monochromatic multi-resolution target is illustrated in FIG. 1. Here the low-resolution portion of the pattern provides data from four 50% duty-cycle white rings and the high-resolution portion of the pattern provides data from 29 peaks and edges.

Figure 2:
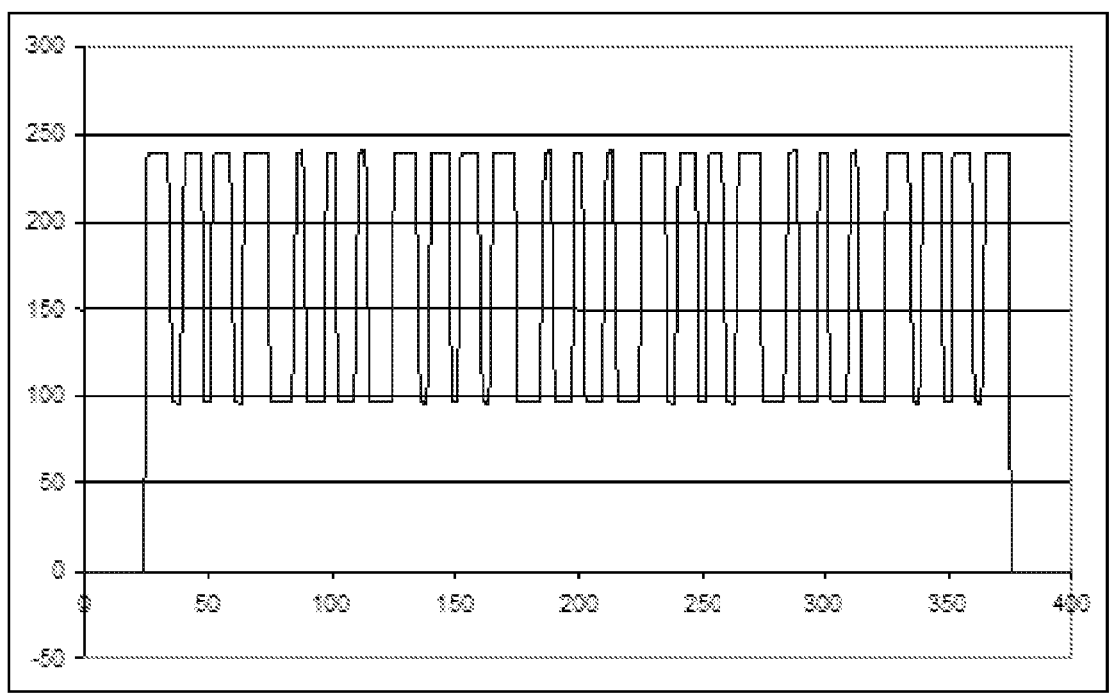
FIG. 2 is a semi-meridian profile of the image of FIG. 1.

The semi-meridian profile from the center to the periphery is shown in FIG. 2.

Figure 3:
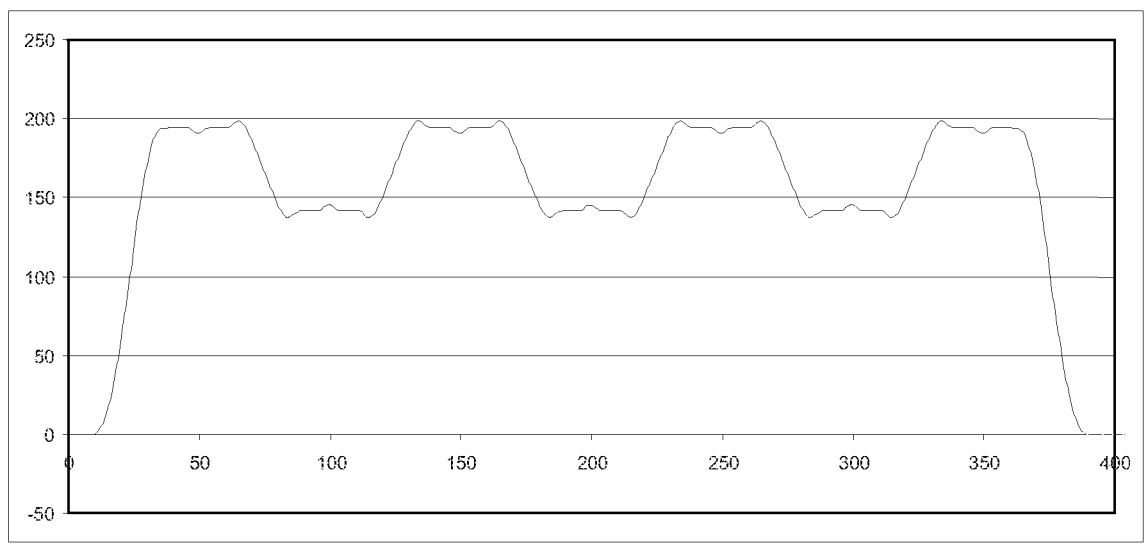
FIG. 3 is a low-frequency components recovered from the multi-resolution profile in FIG. 2.
Figure 4:
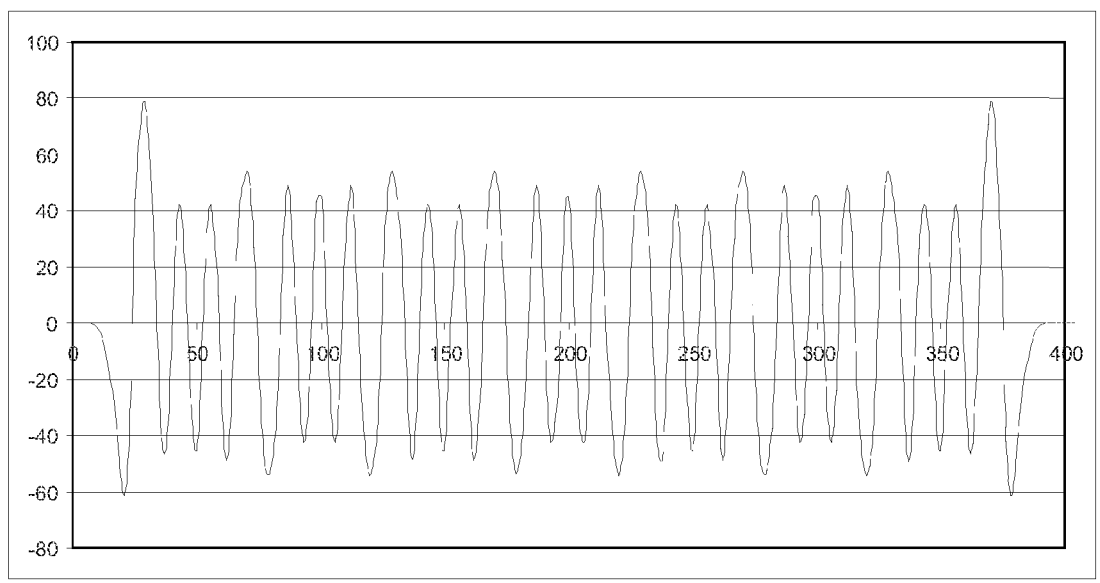
FIG. 4 is a high-frequency components recovered from the multi-resolution profile in FIG. 2.

By properly filtering this profile (using digital filters known to those skilled in the art) the low-frequency and high-frequency components as shown in FIGS. 3 and 4, respectively can be separated.

Using this technique, it is possible to use the multiple resolutions of feature data to detect double reflections as described in U.S. Pat. No. 6,926,408.

The multiple resolutions target also has the benefit of providing a means of adapting the measurements to the surface being tested. For corneas or surfaces with small radius of curvature (high power corneas), the rings will be closer to the center than for larger radius of curvature corneas. If a target has only a large number of rings, the rings can be so close together that they can not be resolved by the subsequent image processing, but the lower resolution rings of the multi-resolution target will still be able to be properly detected so that the surface can be measured. Likewise for a very low power cornea (large radius of curvature), the rings of a typical single frequency target will be spaced far apart so that measurement resolution will be low, but the higher resolution rings of the multi-resolution target will be closer together giving a more accurate representation of the surface. Overall, the multiple resolution target yields higher accuracy measurements and is more likely to obtain measurements for surfaces that could not be measured by typical single frequency targets.

Figure 5:
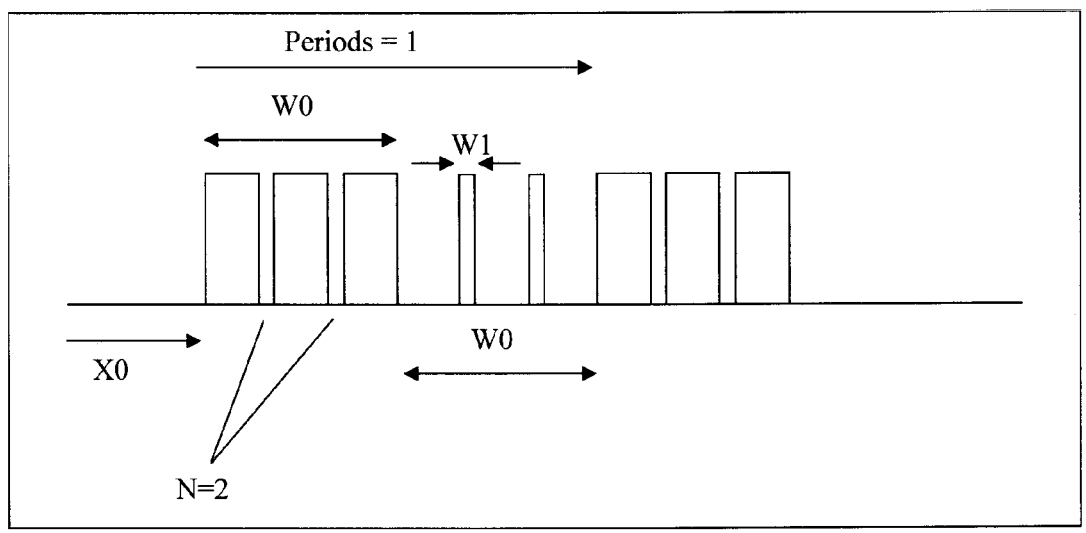
FIG. 5 illustrates the parameters for a preferred embodiment target.

The parameters for an embodiment are illustrated in FIG. 5.

These parameters are:

X0=distance from the center to the first edge of the target.
W0=width of low resolution square pulse.
N=number of high resolution square pulses within a low resolution square pulse.
W1=width of high resolution square pulse.
Periods=number of cycles of low resolution square pulses in the target profile.

For a preferred embodiment, the pattern parameters are:
Low-resolution rings=14
High-resolution rings=52
The coverage of the rings on an 8 mm sphere is:
Peripheral ring radius=4.75 mm
X0=0.5 mm
W0=1.2 mm
Periods=6
W1=0.1 mm
N=3

Figure 6:
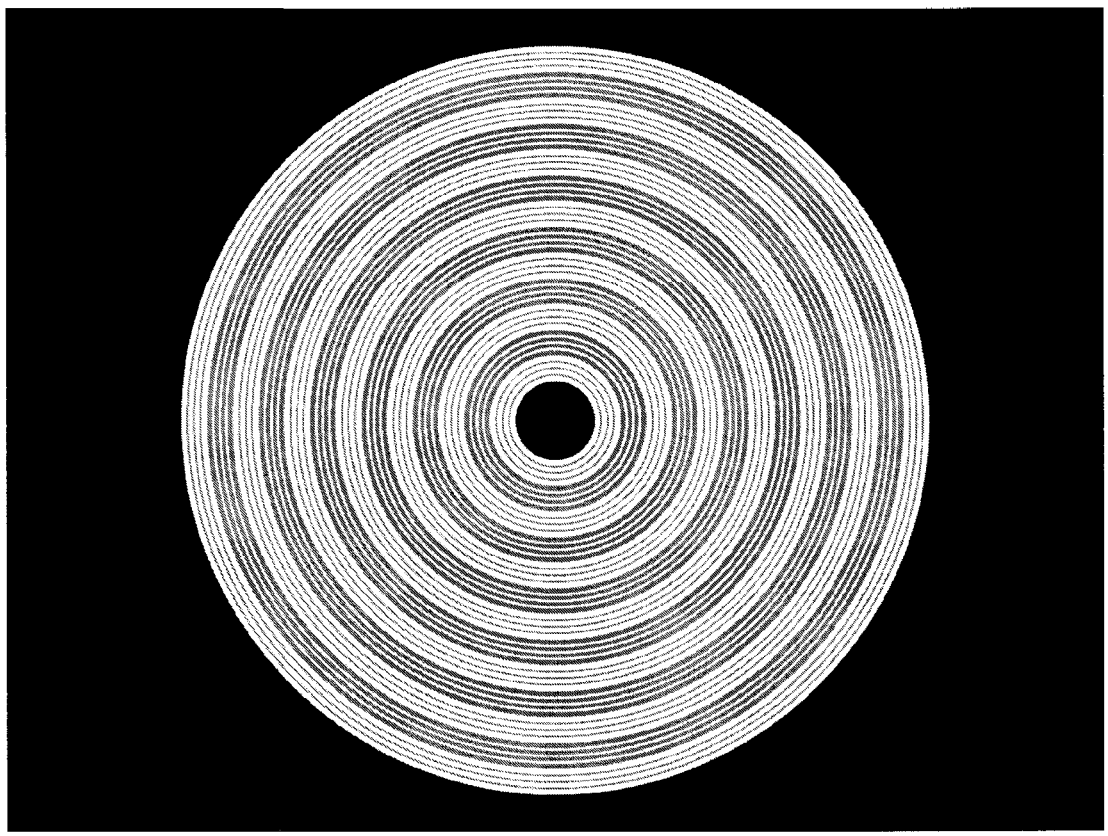
FIG. 6 is a simulated image for a preferred embodiment target.

The simulated image for the captured image of an 8 mm sphere is shown in FIG. 6.

It is understood that the number of low resolution and high resolution rings can be adjusted to suit a particular application and camera resolution.

The target could be manufactured in a number of ways. These include but are not limited to:
1. Place the pattern in front of or combined with an electro luminescent panel.
2. Etch the pattern from a painted diffuse surface which is back lighted.
3. Use side emitting light pipes for each lighted area. Each light pipe could be individually controlled.
4. Use a computer generated pattern such as an LCD or other technology monitor.

Both manufacturing strategies 3 and 4 above provide the ability to turn individual rings ON and OFF so that the correspondence between a feature detected in the captured image and the source of the reflection at the target can be known without any chance for error.

The processing of the captured image involves the typical steps for all concentric ring corneal topographers. Representative processing steps are:
1. Center finding.
2. For each semi-meridian:
   a. Edge detection and peak detection to find the features.
   b. Reconstruction based upon matching detected reflected features and their source point from the target.

Additional steps for multi-resolution targets:
1. For each semi-meridian:
   a. Filtering to separate resolutions.
   b. Detection of multiple reflected features (erroneous reflections). These features include both edges and peaks so that a large number of point correspondences will be available for surface reconstruction.
   c. Reconstructions based upon highest resolution features reliably resolved from the captured image. This is essentially a variable step size algorithm adapted across the regions of the captured image.

Note that unlike single frequency concentric ring target designs, the reconstruction algorithm may make use of low resolution features in one part of the captured image and another higher resolution set of features in another part. This is to take advantage of the highest frequency of data available while ignoring areas with erroneous reflections.

It is also possible to extend the number of resolutions from two to three or more. This can be done by inserting more square pulses within the highest resolution pulses shown in FIG. 5. The resulting processing is the same as before, but now there are three digital filters to extract the ring edge (or peak) features.

It would also be possible to provide multiple monochromatic multi-resolution targets in the same system either via time diversity (each resolution at a different time) or by wavelength diversity (such as described in the U.S. Pat. No. 6,926,408). Another possibility is to provide multiple resolutions according to focal length so that the various frequencies are out of focus for any camera other than the one for which they are designed to be in focus.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

I claim:

1. An corneal topography system for measuring the shape of the cornea of the eye comprising:
   a corneal topographical reflective target;
   a first light source; and
   a device which measures the radius of curvature of the cornea, wherein said corneal topographical target provides a multi-resolution image of multiple resolutions of measurement from a single measurement.

2. The corneal topography system of claim 1 wherein said first light source is a monochromatic light source.

3. The corneal topography system of claim 1 wherein an electroluminescent light is used to form said corneal topographical reflective target.

4. The corneal topography system of claim 1 wherein a diffuse light and a transparent overlay are used to form said corneal topographical reflective target.

5. The corneal topography system of claim 1 wherein said corneal topographical reflective target includes a plurality of concentric rings.

6. The corneal topography system of claim 5 wherein said concentric rings are illuminated and turned off as a group.

7. The corneal topography system of claim 5 wherein said concentric rings are illuminated and turned off individually.

8. A reflective pattern source for use with a corneal topography system for measuring the shape of the cornea of the eye comprising:
   a two dimensional surface, said two dimensional surface having a circular pattern thereon for measuring reflected light from a cornea, said pattern being a function of multiple resolutions of measurements of the shape of the cornea, said multiple resolutions representing at least both the short radius of curvature and long radius of curvature of said cornea.

9. The reflective pattern of claim 8 wherein said pattern is determined by an algorithm.

10. The reflective pattern of claim 8 wherein a monochromatic light source is used to form said two dimensional surface.

11. A process for determining the shape of a cornea of an eye comprising:
    providing multiple resolutions of measurement of the radius of curvature of said cornea from a single measurement.

12. The process of claim 11 including providing a corneal topography target which provides said multiple resolutions of measurement.

13. The process of claim 12 including processing a multi-resolution image from said corneal topography target to enable a measurement of the short radius of curvature of said cornea and the long radius of curvature of said cornea from a single measurement.

14. The process of claim 12 wherein said corneal topography target is formed using a monochromatic light source.

15. The process of claim 12 wherein said corneal topography target is formed using an electroluminescent back light.

16. The process of claim 12 wherein said corneal topography target is formed using a diffuse back light and a transparent overlay.

17. The process of claim 12 wherein said corneal topography target includes a plurality of concentric rings which are illuminated and turned off as a group.

18. The process of claim 12 wherein said corneal topography target includes a plurality of concentric rings which are illuminated and turned off individually.

19. The process of claim 11 including utilizing an algorithm the reconstruct the surface of the cornea in varying resolutions across the measured surface of the cornea.

20. The process of claim 11 wherein the processing of said multi-resolution image from said corneal topography target includes edge and peak detection whereby the total number of measurements from said multi-resolution pattern are increased.

* * * * *